United States Patent
Fulbrook et al.

(10) Patent No.: US 7,967,137 B2
(45) Date of Patent: Jun. 28, 2011

(54) ORGANIZER OF EXPENDABLE SUPPLIES FOR MEDICAL PATIENTS (OESMP)

(76) Inventors: Jason D. Fulbrook, Fairfax, VA (US);
David J. Fulbrook, Fairfax, VA (US);
Jim E. Fulbrook, Fairfax, VA (US)

(*) Notice: Subject to any disclaimer, the term of this patent is extended or adjusted under 35 U.S.C. 154(b) by 0 days.

(21) Appl. No.: 12/155,692

(22) Filed: Jun. 9, 2008

(65) Prior Publication Data
US 2009/0301927 A1   Dec. 10, 2009

(51) Int. Cl.
*B65D 1/34*   (2006.01)
(52) U.S. Cl. ........................ 206/370; 206/564
(58) Field of Classification Search .................. 206/564, 206/557, 562, 565, 570, 571, 363, 370, 438
See application file for complete search history.

(56) References Cited

U.S. PATENT DOCUMENTS

| | | | |
|---|---|---|---|
| 3,802,555 A * | 4/1974 | Grasty et al. | 206/572 |
| 6,253,399 B1 * | 7/2001 | Wagner | 5/507.1 |
| 6,311,841 B1 * | 11/2001 | Hodges | 206/541 |
| 7,523,900 B1 * | 4/2009 | Hlatky | 248/201 |
| 2006/0278785 A1 * | 12/2006 | Wiesner et al. | 248/231.71 |
| 2007/0034767 A1 * | 2/2007 | Mastropaolo et al. | 248/447.2 |
| 2009/0158973 A1 * | 6/2009 | Felterman | 108/102 |

* cited by examiner

*Primary Examiner* — Jacob K Ackun, Jr.
(74) *Attorney, Agent, or Firm* — John Richardson

(57) ABSTRACT

The invention provides a tray organizer apparatus for safely organizing routine expendable medical supplies for in hospital patients disclosing a plurality of variants in the form of a non power embodiment of a surface tray with shaped recesses for retaining medical supplies and power embodiments with 110 ac volt supply with a multiplicity of 110 volt outlet and a plurality of USB ports, Firewire port, and other devices such tiltable LED illuminated mirrors.

The tray organizer is formed of injection molded plastic, folded sheet metal or other equal structures and incorporates a peripheral upstanding rim connected to a lower planar surface from which a number of recessed openings are formed with enclosed bottom surfaces to retain expendable supplies in a variety of shapes.

14 Claims, 5 Drawing Sheets

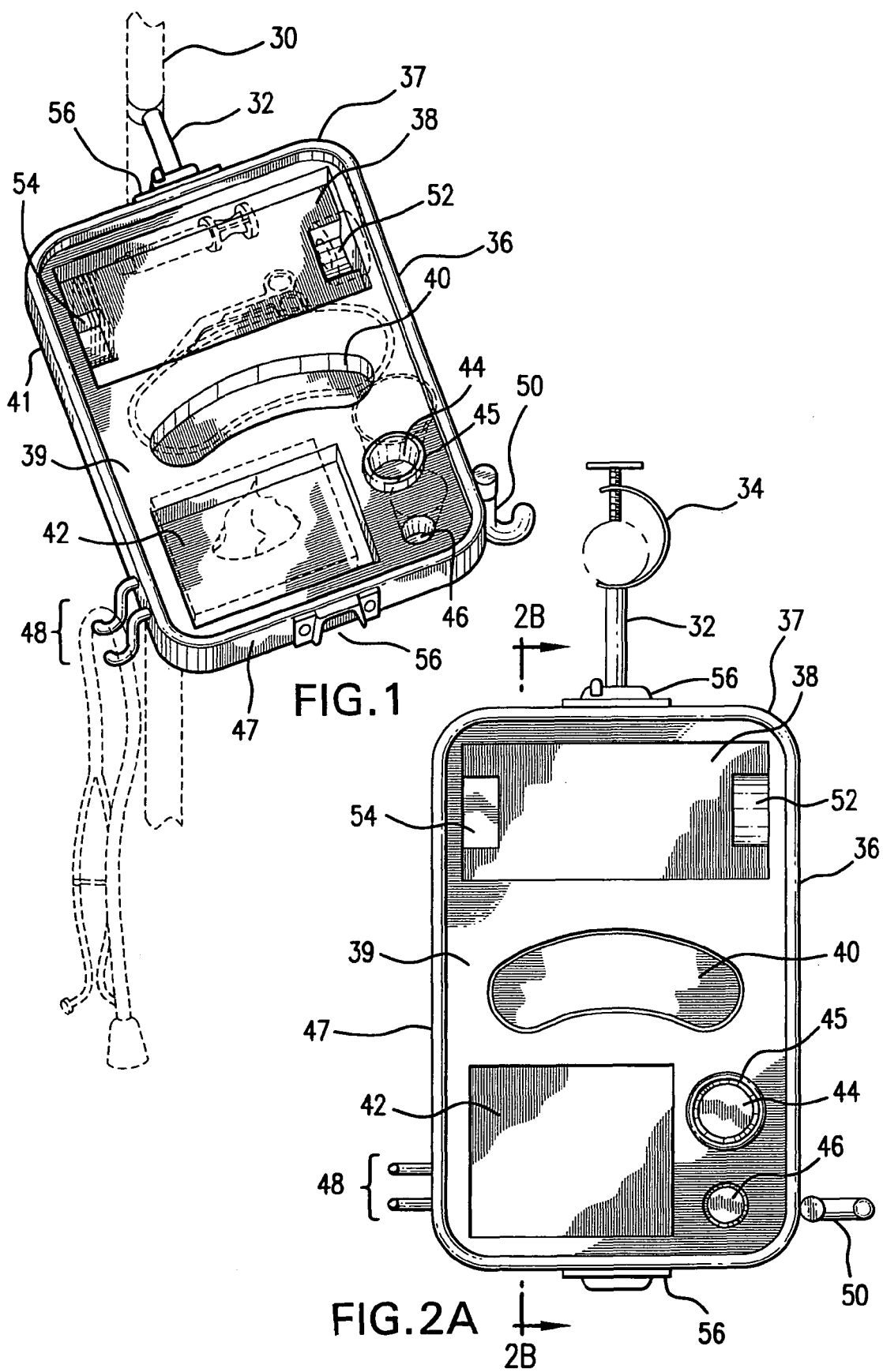

ORGANIZER OF EXPENDABLE SUPPLIES FOR MEDICAL PATIENTS (OESMP)

This Application claims priority to U.S. Design application No. 29/268919 dated Nov. 16 2006.

STATEMENT REGARDING FEDERALLY SPONSORED RESEARCH OR DEVELOPMENT

Not applicable

REFERENCE TO SEQUENCE LISTING A TABLE, OR A COMPUTER PROGRAM LISTING COMPACT DISC APPENDIX

Not Applicable

BACKGROUND OF THE INVENTION

Patient care in a hospital requires medical staff to provide a multiplicity of expendable supplies to patients during confinement to hospital beds and it is both hygienic and effective to ensure that such supplies are well organized, accountable, and efficiently maintained to prevent spread of infection and to provide necessary amenities for the care and convenience of the patient.

Recent developments in medical care settings such as intensive care units have shown a significant increase in the number of patient sensors, monitors and infusion devices for functions such as monitoring heart and ECG respiration rates with oxygen saturation and carbon dioxide levels, taking blood pressure readings, and delivering medications through intravenous (IV) pumps, saline drips, syringe pumps, etc. However, the increase in medical capabilities has also increased the clutter around patients in hospital beds.

Further, it has been reported that cross type bacterial infections contracted in hospital settings are on the increase from categories such as MRSA (methicillin-resistant staphylococcus aureus), VRE (vancomycin-resistant enterococci), and ESBL (extended spectrum beta-lactamase), which contribute to an estimated 19,000 fatalities and 80,000 hospital infections per year. Hence, hospitals must maintain optimal hygienic conditions at all times in all patient care situations.

Medical patients in hospitals, nursing homes, and home care situations routinely use a common set of expendable medical supplies. These supplies can include for example, tissues, a pill cup, a small drinking cup, alcohol wipes, surgical tape, an emesis basin (kidney-shaped container), and other miscellaneous items such as over-the-counter medicines in containers or tubes, syringes without needles for fluid medications, scissors, supplies for IV tubing and connectors, a thermometer, a disposable stethoscope, and any number of other medical products.

Too often these supplies are not organized and tend to be randomly placed on counters, sink areas, night stands, adjustable overbed tables, on the bed itself, and anywhere that seems unoccupied at the time the items need to be set aside or stored. Note that two other expendable supplies used in hospital care include latex gloves and hand sanitizer. However, these two items are usually found in wall-mounted dispensers, not scattered about. Gloves and sanitizer are also used more by care providers and visitors, rather than as patient-use items. Hence, these items are not included in the list of routine expendable supplies that are relevant to the invention described here.

When a bed-restricted patient needs any expendable medical items, if they are scattered about, they may not be located or accessed at arm's reach or as quickly and easily as the situation may require. Even ambulatory patients who can get out of bed too often find accessibility to some items to be inconvenient at the time of need. Most hospital rooms with typical hospital beds also include an overbed table that has an offset vertical base support that adjusts the table surface higher or lower over the bed and has wheels for easy repositioning relative to the bed and patient. An overbed table provides a surface directly accessible to a patient from the hospital bed. However, items on one of these tables can easily fall over or onto the floor because the table tends to become unstable when it is bumped or abruptly moved.

The overbed table, nightstand, and nearby sink or shelf counters are also routinely used for setting non-medical items such as food, drinks, mail, reading materials, toys and games, electronic devices of every type, and personal care items (toothbrush, cosmetics, hair brush, etc.). The unavoidable intermingling of these items creates a disorganized situation that is inefficient and inconvenient for the patient and care providers who have to locate expendable items during routine care procedures. The more disorganized the situation, the easier it is for non-medical and expendable medical supplies to be tipped over or knocked to the floor from any location.

More important, if the expendable items are set upon an unsanitary surface, which happens whenever non-medical items are brought into the hospital room, the items will become dirty and germ-laden, which will expose the patient to other potential diseases and infections. This is particularly important in hospital situations where special care must be taken to avoid germ exposure and unsanitary conditions. The term "germs" of course is common usage and refers to the three most common types of infections, which are caused by viruses, bacteria, and fungi.

When a patient has an infection of one type, they can be vulnerable to additional infections and complications. In humans, white blood cells are important for fighting infection. When a patient has a white blood cell count too low to provide adequate protection to the person, the condition is called Neutropenia. When Neutropenic conditions apply or other diseases that weaken the immune system occur, the hospital room the patient is in must be disinfected and strictly controlled to a greater degree to where special rules are put into effect to minimize infectious disease exposure to the vulnerable patient. Special rules for maintaining patients in more sterile conditions include surgery rooms, rooms for burn victims, intensive care situations, emergency department isolation rooms, some cancer patient situations, and rooms for organ transplant patients. These medical situations require careful control of medical treatment and expendable medical care items to minimize exposure to the patient and maximize convenience and efficiency for hospital care providers, patients, and visiting family members or friends.

The invention described here, which is called the "Organizer of Expendable Supplies for Medical Patients," ensures that a group of typical generic expendable supplies routinely used by patients and care givers for patient care are available in a known location when needed. For simplicity, the "Organizer of Expendable Supplies for Medical Patients" will henceforth be called the "organizer tray." The organizer tray will significantly improve convenience, efficiency, and general comfort for a patient and care providers because most routine expendable supplies will potentially be within easy reach, will be organized together in a known location, the supplies can be readily inventoried and replenished by filling designated slots, and it will be much easier to maintain more hygienic (relatively germ-free) conditions when the expendable items are stored separate from any other unsanitary surfaces or non-medical items that are routinely found in hospital rooms. Spillage will also be reduced, which will further improve hygienic conditions.

Traditional hospital practice has been to provide free-standing trays that can be placed on patient beds to collect necessary expendable supplies in a loose and non-constrained arrangement that is susceptible to mishandling and mislaying leading to placing the patient at risk of infection. The organizer tray will reduce or eliminate non-constrained, random arrangements and improve hygiene control to reduce infection potential.

There are several prior art examples of movable stands and trays attached to intravenous (IV) poles for hospital patient use, such as U.S. Pat. No. 5,114,023, Lavin, providing a flat surface tray attached to a intravenous (IV) pole configured with merely surface cut-outs, U.S. Pat. No. 5,375,604, Kelly et al, provides for a flat surface attached to an intravenous (IV) pole, U.S. Pat. No. 6,969,031, Ugent et al, provides for an obliquely oriented handle coupled to an IV pole provided with an electrical receptacle and power cord. None of these prior art examples provide an organizer that ensures the group of typical generic expendable supplies routinely used by patients and care givers are available when needed in a clean, hygienic, accountable, inventoried and replenishable manner.

To overcome these significant operational limitations and shortcomings in existing prior art in the management and accessibility of expendable medical supplies, the inventive concept described as The Organizer of Expendable Supplies for Medical Patients (OESMP or organizer tray) is disclosed hereunder.

The Organizer of Expendable Supplies for Medical Patients has a multitude of potential applications such as hospital critical care situations, nursing homes, or home health care.

The Organizer of Expendable Supplies for Medical Patients (OESMP or organizer tray) would not require US FDA approval and comprise electrical components that are standard commercially-off-the-shelf (COTS) items, and wherein direct patient intervention and monitoring that impact a patient's status are not applicable for US FDA review requirements.

The organizer tray has numerous convenience features and functions. The organizer tray consists of a molded material that has slots at dimensions that will fit and hold most expendable supply products used by hospitals that include: small boxes of facial tissues, a kidney-shaped emesis basin, a 120 ml drinking cup (equal to four ounces), a 30 ml plastic medicine cup (equal to 30 cc or about one ounce), a roll of surgical tape, and small individual packets of isopropyl alcohol wipes. In addition, the organizer tray comes with hooks for hanging items and a rectangular slot for placing miscellaneous items such as a scissors, a small flashlight (required by the nursing staff during nighttime patient checks), or other medical support items to include over-the-counter medications.

The organizer tray has two embodiments and is shown in the FIGS. 1 to 9. One embodiment has no electrical components (called the non power variant); the other embodiment includes electrical components (called the powered or electrical variant). Three general slot organizations and tray shapes are shown. The organizer tray itself will be composed of an injection molded composite material. Each embodiment or variant has trapezoid or A-shaped metal points affixed to the front and rear sides of the organizer tray. Each embodiment has an attachment assembly that allows the organizer tray to be readily attached and detached to the vertical shaft of an Intravenous (IV) pole so that the organizer tray can be made readily available for patients when an IV pole is being continuously used for patient care.

The organizer tray also comes with two matching C-clamps that can be attached to the A-shaped attachment components in front and rear of the tray so that the tray can be attached to the metal or plastic guard rail found on most hospital beds. Based on a patient's preference for access or a hospital standard operating procedure, the organizer tray can be secured on an IV pole, on the top bed rail when the safety rail is horizontal to the bed and floor, or the IV clamp or bed rail clamps can be detached from the organizer tray so that it can be placed on a flat surface such as an overbed table or nightstand.

Most hospital beds have two bed rails on each side of mechanical beds (four total of equal size). The upper half bed rails provide security for patients from about their waist area up to their head. When a patient raises the bed mattress to become more upright, the bed rail raises parallel with it on most beds because it is attached to the moving frame. The bed rails on the lower half of the bed also move when the mattress is raised as well. However, most patients prefer to keep the lower part of the bed horizontal and only raise the upper bed. In order to use the organizer tray on a bed rail, the rail would have to remain relatively horizontal, as any amount of rising of the rail with the bed would tilt the organizer tray and cause any items stored on it to become unstable. The bed rail clamps would also be attachable to the head or foot boards on some hospital beds, but these locations are less convenient for patients compared to the organizer tray being attached to either an IV pole or a bed rail. Attaching the organizer tray to a bed rail or board is useful, but the caveats for use mentioned here make this configuration less preferable.

SUMMARY OF THE INVENTION

The advantage of the organizer tray being attached to an IV pole is that the tray goes wherever the patient goes such as to the bathroom where expendable items are often required, and the tray is more securely away from surfaces where unsanitary non-medical items would typically be placed. In addition, by mounting the organizer tray on an IV pole or bed guard rail, care providers have the advantage of a standardized location for placing the expendable items listed; it is easier to inventory and replenish the items to ensure they are available, and it is much easier to maintain controlled hygienic conditions such as neutropenic rules when the items are configured to their slots in the tray.

The organizer tray and its components can also be removed with its few components disassembled for cleaning and disinfecting when necessary. The three options for employing the organizer tray on an IV pole, bed rail/board, or flat surface offers significant flexibility. Further the small number of detachable components in this simplistic design makes it easier to account for the items when a configuration change is desired and the configuration options would generally be obvious to the care provider or patient when the organizer tray was set up based on the situation and preference. The design and functionality is so simple and straightforward that minimal instructions will be required, which is also an advantage for users.

BRIEF DESCRIPTION OF THE DRAWINGS

FIG. 1—Shows a pictorial view of the first embodiment of the Organizer of Expendable Supplies for Medical Patients (OESMP) attached to a COTS intravenous (IV) pole in the form of a non power variant. Outline drawings of sample expendable supplies are also shown.

FIG. 2A—Shows a plan view of the first embodiment of the Organizer of Expendable Supplies for Medical Patients (OESMP) attached to a COTS intravenous (IV) pole in the form of a non power variant.

REFERENCE OF NUMERALS USED IN FIGURES

Figure 2B:
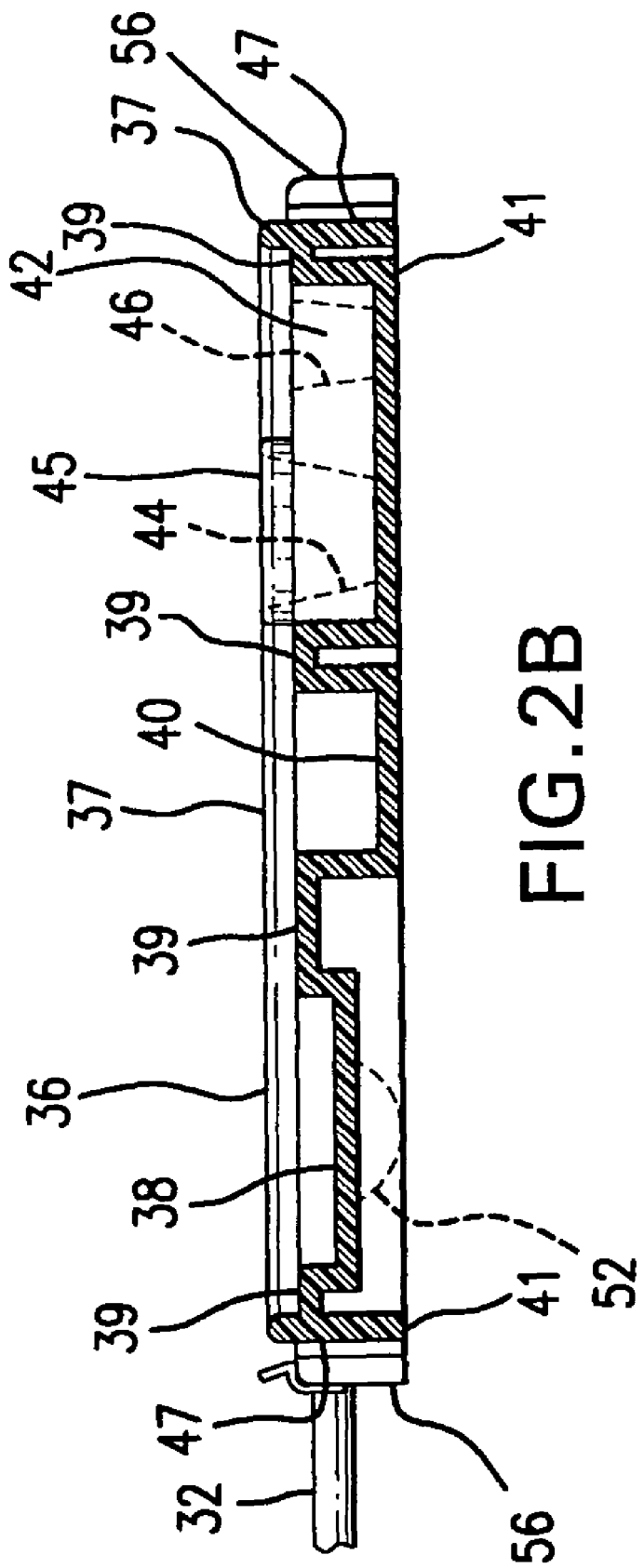
FIG. 2B—Shows a cross-section view of the tray taken along lines 2B-2B in FIG. 2A.

The table below lists all of the reference numerals employed in the Figures, and identifies the element designated by each numeral.

30 COTS vertical telescopic intravenous (IV) metal pole element.
32 IV pole attachment assembly with a telescopic shaft, male attachment assembly and IV pole clamp components.
34 Screw-clamp element for attachment of the organizer tray to the COTS vertical telescopic intravenous (IV) pole element.
36 First embodiment of a non power organizer tray made from materials including folded sheet metal and injection molded plastic, with a plurality of profiled recesses for receiving expendable medical supplies.
37 A tray organizer feature common to all embodiments (first, second, and third) that provides for an upstanding peripheral flange or rim extending above the top surface of tray configured to encompass the entire tray plan profile down to the flat planar surface 39 from which the recessed openings 38, 40, 42, 44, 46, are constructed with enclosed bottom surfaces.
38 Rectangular shaped profiled recess with a plurality of semi-circular deep recess and rectangular profiles for receiving expendable medical supplies such as surgical tape, isopropyl alcohol wipe packets, scissors, and more.
39 Upper Flat planar surface common to all three embodiments from which the recessed profiled openings are formed with enclosed bottom surfaces.
40 Elliptical arc shaped profiled recess for receiving expendable medical supplies such as an emesis basin.
41 Flat bottom surface of tray composed of the periphery 47, enclosed planar bottom surfaces 37 of recesses 40, 42, 44, 46, 52 and 56.
42 Rectangular shaped profiled recess for receiving expendable medical supplies such as a small box of hospital COTS tissues.
44 Large circular shaped recess for receiving expendable medical supplies such as a 120 ml (4-ounce) drinking cup.
45 Upstanding rim configured to encompass circular shaped recesses 44.
46 Small circular shaped recess for receiving expendable medical supplies such as a 30 ml (1-ounce) pill cup.
47 Outer periphery of tray that is continuous with upper flat surface 39 and rim 45.
48 Double hooks attachment where the bottoms of the hooks are on the same plane as the tray bottom to allow the tray to sit flat on another flat surface.
50 Hinged single hook attachment that allows the hook to be rotated to the side when the organizer tray is placed on a flat surface.
52 Semi-circular shaped recess for receiving expendable medical supplies such as a roll of surgical tape.
54 Small rectangular shaped recess for receiving expendable medical supplies such as a number of small packets of isopropyl alcohol wipes.
56 Female element of the attachment assembly.
57 Second embodiment of power variant organizer tray made from materials including folded sheet metal and injection molded plastic with a plurality of profiled recesses for receiving expendable medical supplies.
58 Power cord plugged into organizer tray socket.
59 Large rectangular shaped recess for receiving miscellaneous items and expendable medical supplies on the power variant organizer tray.
60 USB (Universal Serial Bus) port (5-volt power source).
62 Standard three-hole, 110-volt outlet.
64 Firewire port (IEEE 1394 interface, 30-volt power source).
66 On/off slide switch for LED (light emitting diode) light.
68 LED light unit.
70 Hinged back plate that allows plate to rotate forward about 45 degrees or back about 25 degrees from its vertical position.
72 Rectangular mirror on back plate.
74 Male part of the attachment assembly.
76 Male attachment assembly latch.
78 Screw-clamp assembly for bed rail or head/foot board attachment.
79 Third embodiment of power variant organizer tray made from materials including folded sheet metal and injection molded plastic with a plurality of profiled recesses for receiving expendable medical supplies.

DESCRIPTION OF THE PREFERRED EMBODIMENTS

The instant invention incorporates a number of elements that can be categorized as commercially off-the-shelf and these are identified accordingly as COTS. The novel features of the instant invention incorporate organizer trays for holding/securing/locating a plurality of expendable supplies for bed-ridden patients in hospital or home care settings and are provided in a number variants embodying non power and power versions. All the tray embodiments incorporate molded formats with peripheral upstanding rim portions 37 encompassing profiled recessed openings 38, 40, 42, 44, 46, formed in a lower planar surface 39 with enclosed bottom surfaces for holding expendable medical supplies.

As stated, the organizer tray described here has three primary embodiments: one without electrical components (non power variant) and two with electrical components (power variant). The first embodiment is composed of all of the features listed above and is shown in FIGS. 1, and 2. Since this embodiment is composed of only the composite material tray and attachment accessories, the device can be more easily disinfected, even in an electronic and heated immersion washing or disinfecting system. This embodiment would be more useful when the most stringent neutropenic and hygienic hospital room conditions apply because of its simpler design and ease and advantage for disinfecting. In addition, when electromagnetic interference (EMI) from non-essential electronic devices may be a factor or restriction in some patient care situations, the non power variant would be the best choice for use.

Figure 3:
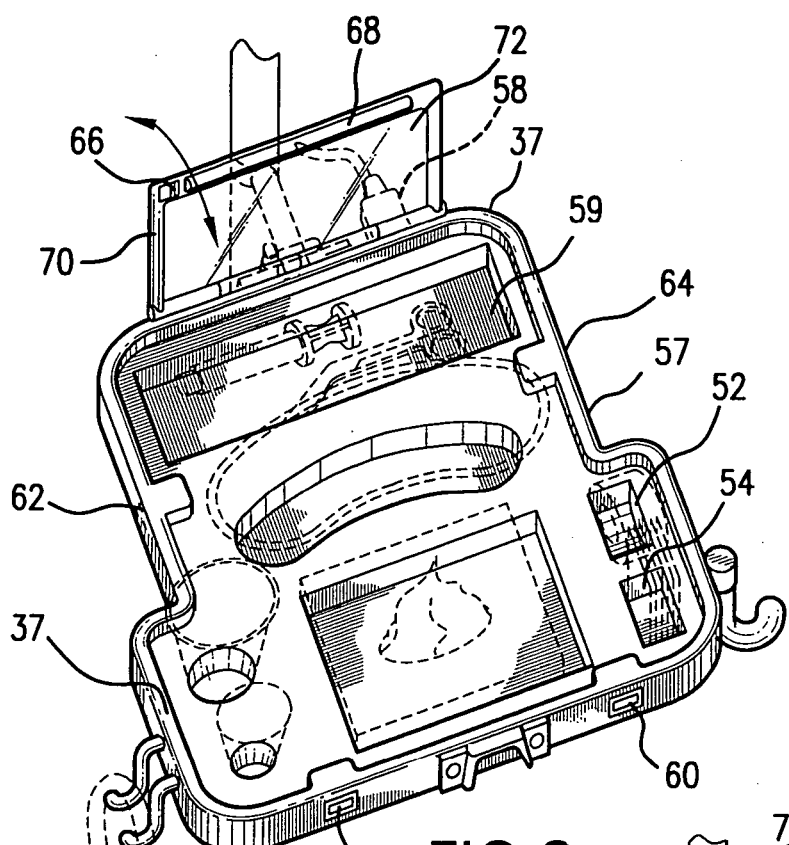
FIG. 3—Shows a pictorial view of the second embodiment of the Organizer of Expendable Supplies for Medical Patients (OESMP) attached to a COTS intravenous (IV) pole in the form of a power variant. Outline drawings of sample expendable supplies are also shown.
Figure 4:
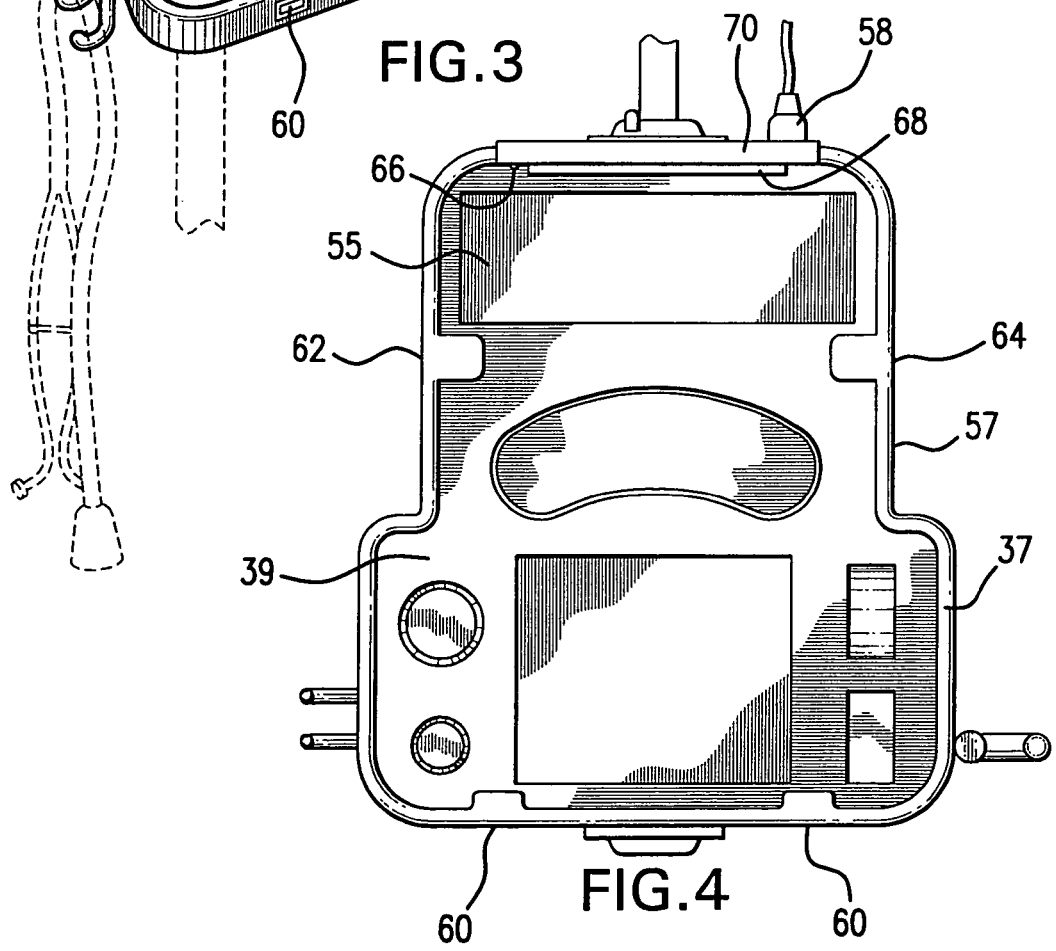
FIG. 4—Shows a plan view of the second embodiment of the Organizer of Expendable Supplies for Medical Patients attached to a COTS (IV) pole (OESMP) in the form of a power variant.
Figure 5:
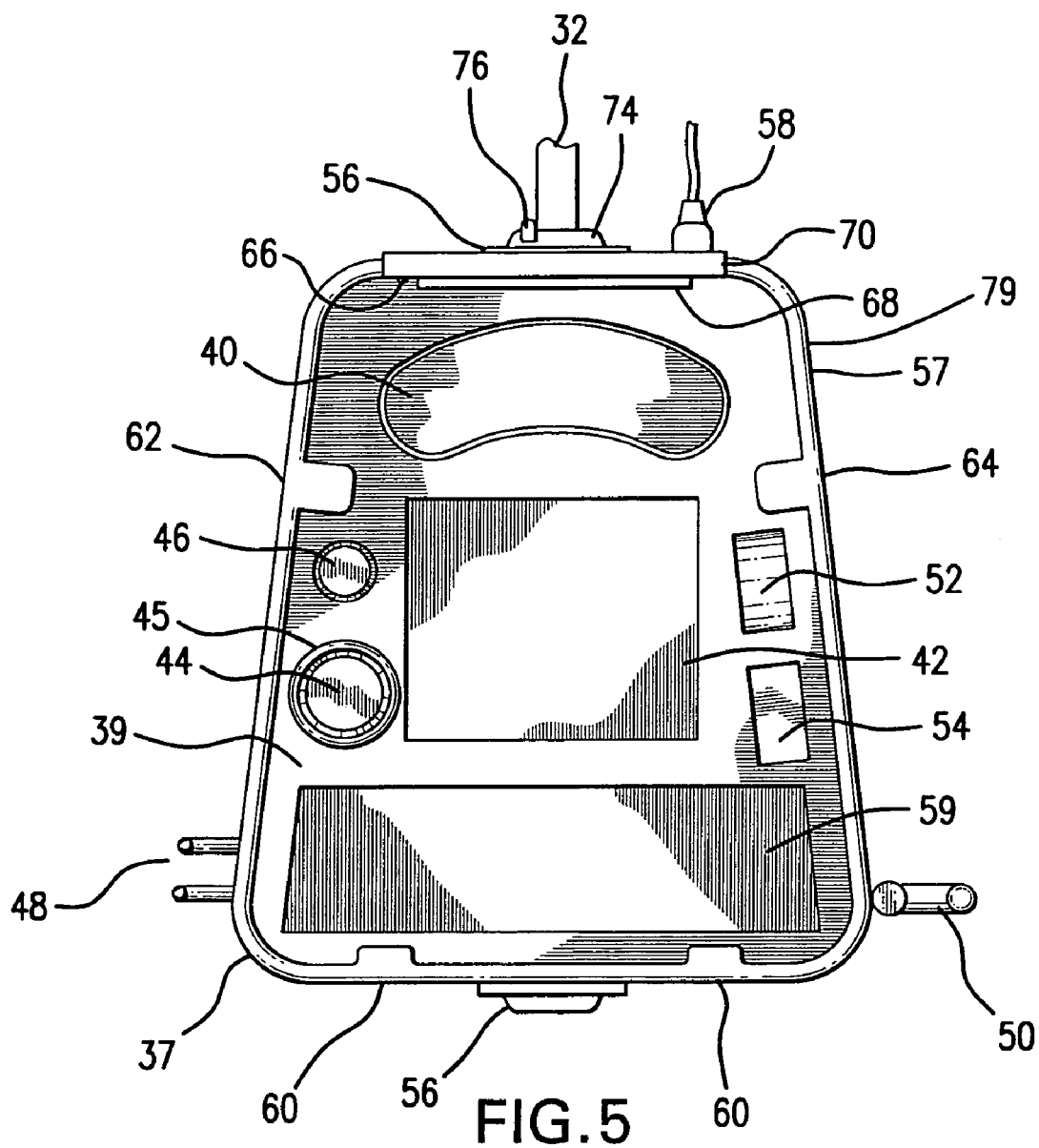
FIG. 5—Shows a plan view of the third embodiment of the Organizer of Expendable Supplies for Medical Patients (OESMP) attached to a COTS (IV) pole in the form of a power variant, wherein the recessed slots are placed differently from the slots shown in FIGS. 3 and 4.
Figure 6:
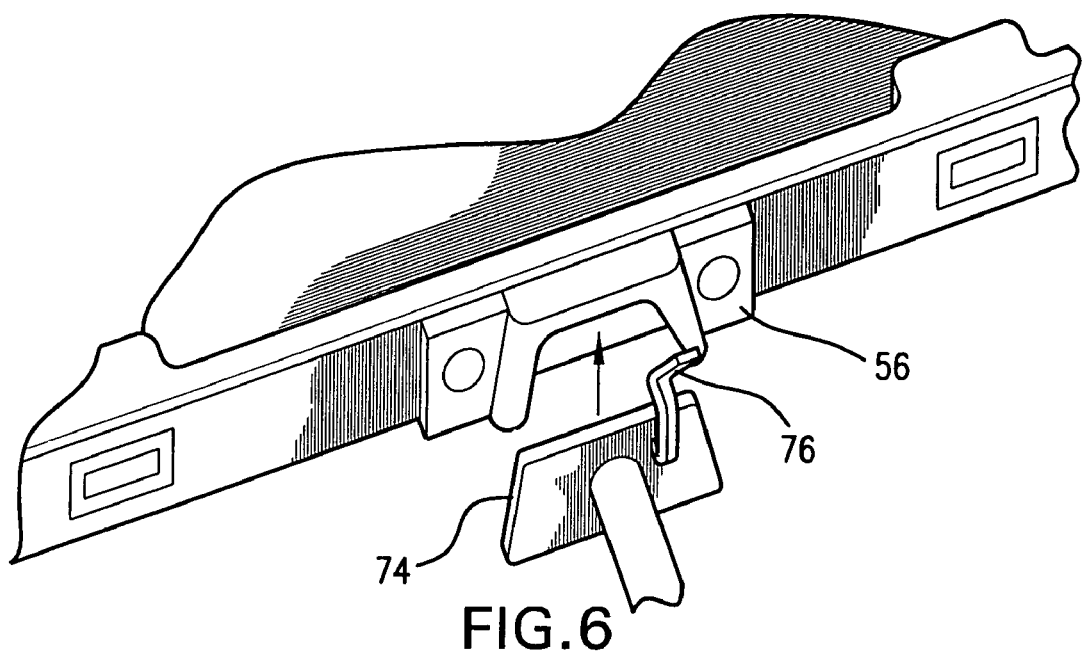
FIG. 6—Shows a pictorial view of the attachment assembly with female component being part of the organizer tray and the male component being part of an IV pole attachment assembly.
Figure 7:
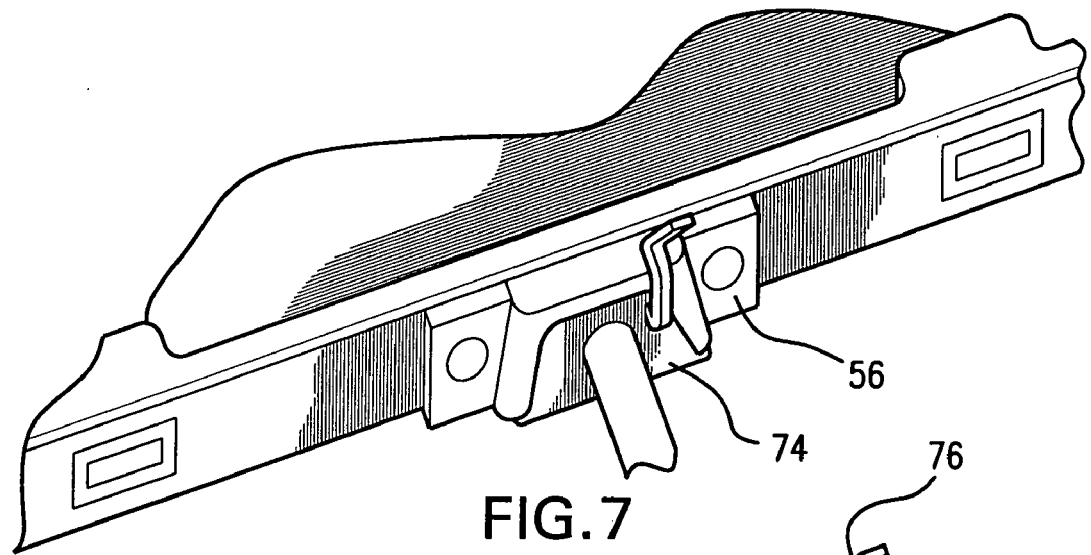
FIG. 7—Shows a pictorial view of the organizer tray attachment assembly with male and female components snapped together and secured by a latch.
Figure 8:
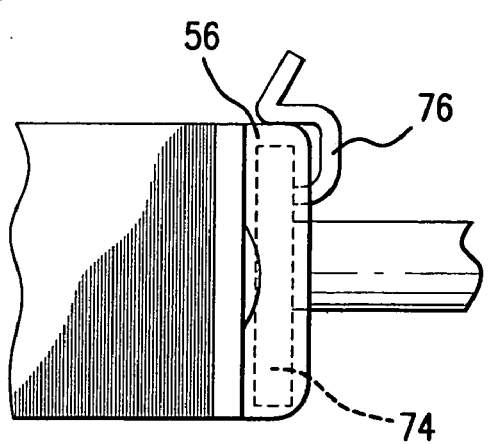
FIG. 8—Shows a side pictorial view of the organizer tray attachment assembly.
Figure 9:
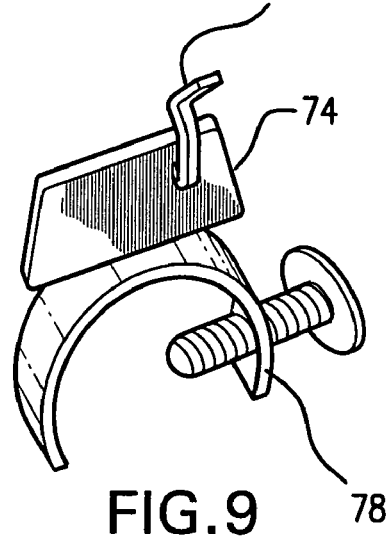
FIG. 9—Shows a pictorial view of the male assembly for attaching the organizer tray to a hospital bed rail or head/foot board by latching one assembly each on the front and rear of the organizer tray.

The second embodiment has all of the features and functions of the first embodiment, but a plurality of electrical components are added to the power variants, as well as a mirror in the back that can tilt forward and back from vertical as desired by the patient. This embodiment is shown in FIGS. 3, 4, and 5 and the electrical components include a 58 socket to attach a power cord (cord included), a standard 110-volt three-hole socket 62 (grounded outlet), two Universal Serial Bus (USB) sockets 60 (to provide 5-volt, 500 mA power), one FireWire socket 64 (IEEE1394 connector port to provide 30-volt, 1.5 A power), and a small vanity light 68 with an on/off slide switch 66 as part of the mirror assembly 72. The USB and Firewire ports will supply power only and will not transfer data, which is their other critical function when used in computer and data network systems. The electrical components of the powered organizer tray will conform to the highest industry and government safety standards for devices of this type.

The third variant is the third embodiment of another power variant shown in FIG. 5, which has a more compact design and a different arrangement of recessed elements for receiving expendable supplies. Again, the electrical components include a socket to attach a power cord 58 (cord included), a standard 110-volt three-hole socket 62 (grounded outlet), two Universal Serial Bus (USB) sockets 60 (to provide 5-volt, 500 mA power), one FireWire socket 64 (IEEE1394) connector port to provide 30-volt, 1.5 A power), and a small vanity light 68 with an on/off slide switch 66 as part of the mirror assembly 72. The USB and Firewire ports will supply power only and will not transfer data, which is their other critical function when used in computer and data network systems. The electrical components of the powered organizer tray will conform to the highest industry and government safety standards for devices of this type.

The aforementioned electrical outlets provide easy access for patients and care providers with common voltage source connections in order to charge and power electronic conveniences such as cell phones, iPods, MP-3 players, a personal digital assistant (PDA), a Blackberry, Bluetooth headsets, and any number of other devices that require low voltage sources or a 110-volt outlet. The 110-volt socket also provides a means to connect devices that have an AC/DC converter power source.

The addition of a variety of electrical sockets or ports to the power organizer tray in embodiments two and three are useful for the convenience and morale of patients, although low voltage or AC to DC converted medical devices such as syringe pumps could also be readily connected to the electronic organizer tray embodiment, which offers a highly convenient and effective option when desired or required in patient care situations. It is envisioned that the hooks and miscellaneous slot in the organizer tray could be used for holding either medical devices or personal electronic devices, and that these devices can be cleaned using disinfectant wipes in order to maintain as clean an environment as possible. Clearly, the hooks and miscellaneous tray offer medical and non-medical options and the degree of either neutropenic or hygienic control would determine the acceptability of mixing expendable medical items and non-medical items on the tray.

The organizer tray embodiments one, two and three are flexible in how these individual variants can be used. When desired, the organizer tray can be lifted from the IV pole attachment assembly by pulling the flexible latch back to release the male element of the assembly from the female element on the tray in order to place the tray on a flat surface such as an overbed table. Unfortunately, most overbed tables are also somewhat unstable and experience has shown that loose items too often can be knocked off the table surface from abrupt movements of the table or by one item interfering with the other. Drinking cups and pill cups are especially vulnerable to being knocked over on overbed tables and once any item falls to the floor, it must be discarded when neutropenic or other isolation rules are in effect. Further, when drinking cups, cold containers of drinks, and ice bags (or hot water bags) are kept on the overbed table or any nearby adjacent surface, visible moisture and wetness can form on the surfaces, which also cause problems for maintaining hygienic conditions, and such problems cause general annoyance for patients. Hence, any device which adds stability and reduces the potential for mishaps provides an advantage to the patient and care providers.

One might argue that the better design for a tray would be to have one single large recess for miscellaneous items or a series of generic slots or cutouts, as is evidenced by some devices in the prior art. However, the organizer tray has generic recessed slots and slots designed for designated expendable items because this design adds stability and security and organization to the placement of the items and because the ability to identify, inventory and replenish standard use expendable items is a major advantage over purely generic trays or tables.

It is important to note that the placement of slots for identified items is ergonomically determined and not random. While there are innumerable options in how the expendable items may be organized as shown in FIGS. 1, 3 and 5, the configurations shown in FIGS. 1 and 3 are ergonomically determined to be more usable than some other configurations. For instance, patients use tissues more frequently than any expendable supply, as they have innumerable uses. The typical box of tissues used as expendable items in hospitals also has a relatively low height profile, so placing this most used item in the front does not obstruct items toward the back of the tray. Because the tissue boxes may sit higher than other items such as alcohol wipes or a scissors in the miscellaneous recess, one could argue that this item should have been placed in the back of the tray. However, this would obstruct the mirror in the electrical embodiment and when reaching for tissues, potential interference with this action could occur each time the patient's hand passes over the other items. Further, the smaller pill cup is placed in the smaller round recess in front of the drinking cup (larger round recess) for ease of reach and visibility to the patient. After some trial and error, the organizations as shown in the embodiments are preferable over other configurations. Hence, the disclosure hereto does not designate a precise configuration for either the non power first embodiment, or electrical (powered) second and third embodiments, but a preferred ergonomic configuration is shown in the embodiments shown in FIGS. 1, 3 and 5.

When a patient is moved from his/her room, there are IV poles that can be attached directly to the bed head board area, rather than the free-standing type with wheels and an adjustable vertical telescoping shaft. In this case, items on the free-standing IV pole can be temporarily transferred to the bed-attached IV pole. In this case, the organizer tray can also be included with the other transferred medical items as long as there was still room on the shorter bed-attached pole. If there is not room, then the organizer tray could be removed from the standing IV pole and attached to the lower bed guard rail for continued access. Some hospital beds allow for multiple IV pole attachments to the head or foot board areas. In this case, an organizer tray could be attached to one of these attachment IV poles for routine use. Since the tray attachment assembly has a telescoping shaft that allows it to be moved farther out from the IV pole vertical shaft, the tray would still be within easy reach for access by patients and care providers. This option is another useful alternative when the free-standing IV pole is overloaded with medical items or less convenient to the patient, but the preferred use is still as an attachment to a free-standing IV pole.

Some additional emphasis also needs to be noted concerning the advantage of the organizer tray as an IV pole attachment accessory. Too often patients must go from their beds to a portable toilet, separate bathroom or shower/bath, or the patient needs to be moved to another part of the hospital for some type of treatment or test while remaining tethered to an IV pole to receive some type of continuous or periodic IV fluid or medication. During these times, patients require expendable supplies more than at other times and by having them available, the patient gains a significant amount of independence along with the convenience and efficiency advantages that also apply to care providers to respond to patient needs.

Earlier it was noted that latex gloves and hand sanitizer pump containers are common expendable items used for patient treatment, but these items are frequently wall-mounted in hospital rooms. Regardless of the location of gloves or sanitizer, single or pairs of gloves or a small hand sanitizer container could also be readily placed on the miscellaneous slot of the organizer tray for convenience when desired. So, it is apparent that the utility of the organizer tray goes well beyond the designated tray slots.

The addition of electrical component features to the organizer tray has a number of clear advantages in functionality. For example, the embodiments provide the convenience of electrical outlets 62 for 110-volt and low voltage systems 60, 64 (5-volt USB, and 30-volt FireWire ports) that patients need to power their cellular phones, iPods, etc. for entertainment and to stay in touch with relatives and friends during hospital stays. Specifically the disclosed plurality of outlets is handy and provides a relatively universal set of power options to accommodate most low-voltage electronics systems along with the 110-volt outlet. The power organizer tray includes two USB ports 60 because of the high number of low-voltage devices frequently used by people today. The USB 60 and Firewire 64 ports will likely become more useful in the future as more COTS devices become available for people that can be powered by such connection ports. In the future, more medical devices such as syringe pumps will be sold that include connectors for the established low-voltage USB and Firewire ports as well.

In addition, the mirror and vanity light provides the means to accommodate the majority of patients who want or need to see what they look like from time-to-time and being bed-restricted makes this action very difficult unless a hand mirror is provided to the patient. The vanity light 68 can also serve as a night light or temporary light source when care providers must make nighttime visits to the patient to check vital signs, or deliver or change medications required by a treatment protocol. The light 68 also provides illumination for locating the expendable supplies when needed.

The benefit of the organizer tray is as important to the care provider as it is to the patient and emphasis must be placed on the advantage of being able to move the collection of selected expendable supplies in one action to another location on or off of the IV pole, flat surface, or bed rail when required or desired. As stated, the organizer tray includes recesses that are best suited to a chosen group of expendable supplies. For instance, the rectangular recess 42 is sized to fit square and rectangular boxes of tissues commonly available as COTS expendable supplies. The emesis basin, drinking and pill cups, alcohol wipes, and surgical tape are all standardized COTS items of similar dimensions regardless of the supplier/manufacturer. Latex gloves and hand sanitizer dispensers are not included on the organizer tray because these items are typically available from wall or counter dispensers, although a pair of latex gloves and a small bottle of hand sanitizer could be placed in the miscellaneous slot of the organizer tray. The miscellaneous recess and hooks add flexibility to the overall design of the OESMP.

It will be evident to those skilled in the art that the organizer tray has another advantage in that it designates expendable items intended for the patient. When neutropenic and hygienic rules apply, separate items that may be used by visitors or care providers can be placed on non-sanitary surfaces with less worry that they will contaminate the expendable items reserved for the patient. For instance, too often visitors require tissues for their own use and if they handle the tissue box from the organizer tray, some contamination could occur that is best avoided. So, once again the organizer tray creates a recognized zone or location where neutropenic or other hygienic control rules can be better and more effectively applied and complied with, which would reduce the number of inadvertent secondary infections that occur too often in hospital environments.

The organizer trays of all the embodiments can be composed of a variety of materials including folded metal, or injection molded composite materials or equal materials of light weight that may be readily disinfected. In the non power variant, the tray can be easily cleaned by disinfectant wipes or fully immersed in hot water, or placed inside a system that cleans, disinfects, and even sterilizes the organizer tray. The power variant embodiments two and three of the organizer tray cannot be immersed in fluids or placed in a cleaning system without risking a short of any of the electrical components. Cleaning these variants require the use of small isopropyl alcohol wipes or some other type of recognized cleaning and disinfecting solvent. The organizer tray surfaces are smooth and the recesses have smooth edges as well to facilitate cleaning. The non power tray variant embodiment one will not have a closed internal compartment and will have a much lighter composite material weight than the power organizer tray; whereas the power tray will have a sealed bottom and higher weight necessitated by the electrical components and the need to protect users from exposure to said components.

In order for the organizer trays to be used on a flat surface, the bottom of the molded tray must also be flat in both the open non power and power variants of the organizer tray. The non power tray may have an open bottom, but the sides will allow the tray to sit flat on a flat surface. The non power and power organizer trays have a single hook on one side and a double hook element on the other side toward the front. The single hook is attached to the tray body by a rivet or other known means so that it can rotate clockwise or counterclockwise in order to move the lower part of the hook up enough to raise it above the bottom of the tray; thus allowing the tray to sit flat. The double hook arrangement is not movable and is attached to the top of the organizer tray body. The lower hooks of this element do not go below the bottom of the tray so they too will not interfere with the tray being placed on a flat surface.

All the embodiments of the organizer tray provide universal application to all hospital environments and specialty care areas, especially where neutropenic or sterility rules apply in rooms such as those used for operations, intensive care, transplants, cancer, burn, pediatric, and emergency isolation situations. The organizer tray also has uses in any type of intermediate and home care acute or chronic patient situations where an IV pole or hospital bed is employed, or the tray may be used on a flat surface in any environment when IV poles and hospital beds are not employed.

The first, second and third embodiments tray variants can be arranged for attachment to COTS IV portable telescopic poles by means of attachment assembly 32 and a screw-clamp element 34.

The first, second and third embodiments tray variants can be arranged for attachment directly to a bed head or foot boards, side rail by means of a female attachment connected 56 by bolts, rivets, or other equivalent means to the said tray which is in turn connected to a male connector 74 and held in place by an assembly latch 76. The final connection to the said bed head, side rails is by means of a screw-clamp 78.

In the power variant, the Universal Serial Bus (USB) 60 is an industry standard port designed to connect peripherals such as mice, keyboards, scanners, digital cameras, printers, hard disks, and networking components to a personal computer (PC). The USB 60 has four pins in its connector: two are for data transfer; the other two are for power and ground, which provide 5 volts DC at 500 mA. The USB ports 60 on the power organizer tray provide power only and will not support data transfer. A maximum of 5 volts is sufficient to power many small, personal electronic devices such as iPods, MP3 players, some cell phones, and more. Some medical devices such as syringe pumps operate on low voltage and may be adopted to operate from USB ports 60 in the future, so this port is useful for numerous purposes as a power source.

The Firewire port (IEEE 1394 interface port) 64 was developed by Apple, Inc. The Firewire port on the power organizer tray will have the standard 6-pin connector that can provide 8 to 30 volts at 1.5 A maximum. Two of the pins in this port will provide the voltage and ground while the other four data pins will be inactive. Firewire connections are becoming increasingly popular for interfacing with small electronic devices in part because the power source is higher and thus can power more peripheral devices and can charge some devices that have rechargeable batteries. In the future, low voltage medical devices will probably have connectors to interface with Firewire ports as well, especially because of the higher voltage source of Firewire over USB ports.

As stated, the organizer tray will preferably be produced from an injection mold and will be composed of a composite material that is resistant to high temperatures and cleaning solvents, and which offers a high durability. In the alternative the organizer tray can be constructed from materials such as stainless steel, metallic alloy steels and equal materials exhibiting non surface oxidizing properties. The inside of the power organizer tray variants in the second and third embodiments will include standard COTS AC to DC converters that will reduce the voltage going to the USB ports to a maximum of 5 volts (500 mA) and a maximum of 30 volts (1.5 A) to the Firewire port. The COTS electrical components and circuit design will comply with all industry and government standards for safety and defined use applicable to the powered organizer tray.

Two USB ports 60 are positioned and connected integral with an internal voltage conversion unit for the purposes of powering devices such as PDAs, MP3 player, iPods or equal electronic devices.

A Firewire port 64 is positioned and connected integral with an internal voltage conversion unit for the purposes of powering and recharging devices such as PDAs, iPods, MP3 players, cell phones, or equal electronic devices.

Positioning of typical COTS 110-volt grounded outlet 62 and an AC to DC power converter unit connected from the power cord outlet.

The hinged back plate 70 with mirror 72 and LED light 68 is provided with an on/off slide switch 66. The said back plate is hinged at the base so that it can be rotated forward and backward (from front to rear).

As will be evident from FIGS. 1 and 2, the non power embodiment of the OESMP has the following significant advantages over the existing prior art:

1. The inclusion of recessed slots/profiled openings tailored to fit routinely used COTS expendable medical supplies, wherein the said recessed slots are formed in a tray upper planar surface 39 with enclosed bottom surfaces 41 for item retention purposes, and with a peripheral upstanding flange or rim portion 37 which may be up to one inch high that is continuous with peripheral surface 47, and that ensures loose materials such as, ballpoint pens, writing pens, pencils, reading glasses, etc do not become loose and dislodged.
2. The inclusion of elements that allow the organizer tray to be effectively used as an attachment to an IV pole, as a tray placed on a flat surface, or as a tray attached to a hospital bed guard rail or head/foot board.
3. The ability to wash and sterilize the non power organizer tray and its components by immersion in cleaning systems or fluids allows the apparatus to be better cleaned, disinfected, or even sterilized in order to provide a more germ-free area to place expendable medical items.
4. A design that allows rapid inventory and replenishment of expendable medical supplies in a dedicated space that greatly improves efficiency and convenience for patients and care providers.
5. A telescopic shaft as an element of the IV pole attachment assembly that allows the organizer tray to be placed closer or farther from the IV pole vertical element to optimize stability, convenience, and reduce obstruction with other medical care systems or non-medical devices and systems.
6. A fixed adjustable, stable flat surface attached to a COTS IV pole ensures accessibility to needed re-usable medical supplies by the caregiver and the patient on as-needed basis.
7. A flat surface removable from the IV pole to ensure accessibility to needed re-usable medical supplies by the caregiver and the patient on as-needed basis.
8. Provides an efficient, economical means for locating and securing items in recessed, defined and tailor made spaces for re-usable medical supplies in hospital and non-hospital room settings where patient care occurs.

9. A single and paired hook attachments to sides of the organizer tray structure to facilitate securing medical devices such as stethoscopes, bed-pans, and urinal pans, ice bags, hot water bags or a variety of non-medical personal devices.
10. Provides a means for locating in a readily accessible manner a variety of medical paraphernalia.
11. A plurality of recesses of varying circular openings (diameters) in the form of cylindrical vertical shapes for receiving and supporting cylindrical objects, such as drinking cups, pill cups, cold containers for drinks, etc.
12. Rectangular shaped recessed openings for securing appliances such as syringes, scissors, and re-usable supplies such as surgical tapes, and other miscellaneous items.
13. Kidney-shaped recessed opening for devices such as an emesis basin (used when patients need to vomit or simply spit something out).
14. Square or rectangular shaped recessed openings for facial tissue box, small packets of isopropyl alcohol wipes.
15. Small lip 45 surrounding circular openings 44, 46, to prevent drinking cups being dislodged.

It will be clear from FIGS. 1 and 2 comprises a plurality of features to achieve the desired invention objectives and by way of enabling disclosure these are identified in the following:
1. Securing metal clamp 34 for attaching to COTS IV metallic pole.
2. Flexibility to provide a flat bottom surface 41 either attached to an IV pole or free-standing on a bed or bedside cabinet.
3. Provision of ready attachments to bed head or foot boards, or bed rails by means of specific male 74, female attachments 56, latch 76 and screw-clamp 78.
4. Provision of upstanding rim 37 encompassing the complete periphery 47 of the three tray embodiments to ensure that the expendable medical supplies are held and retained in assigned recessed openings located in the upper tray planar surface 39 and that loose standing materials positioned on the said planar surface are restricted from rolling or sliding off.
5. Provision of a plurality of recessed openings 38, 40, 42, 44, 46, to hold and retain a variety of expendable medical supplies for the ready use by patients in hospital and homecare settings.
6. Provision of an upstanding rim 45 that encompasses recessed opening 44 for the purpose of raising the height of the recess to better secure an expendable drinking cup.

It will be clear from FIGS. 3, 4 and 5 that the power embodiment of the organizer tray comprises a plurality of features to achieve the desired invention objectives and advantages over prior art by way of enabling disclosure that are identified in the following:
1. The availability of the relevant features 1-15 detailed in [0064] for the non power variant.
2. Electrical outlets/ports as power sources (62, 110-volt, 60, USB, 64, Firewire).
3. LED night light illumination source 68 with on/off switch 66 on back plate.
4. Adjustable mirror 72 on back plate of organizer tray.
5. By removing the power cord from the organizer tray socket, the tray can be used as a non power tray when necessary.
6. Cleaning and disinfecting will be accomplished by hand using disinfectant wipes or other cleaning agents.
7. A fixed adjustable, stable flat surface attached to a COTS IV pole ensures accessibility to needed re-usable medical supplies by the caregiver and the patient on as-needed basis.
8. A flat surface removable from the IV pole to ensure accessibility to needed re-usable medical supplies by the caregiver and the patient on as-needed basis.
9. Provides an efficient, economical means for locating and securing in recessed tailor made defined space openings for re-usable medical supplies in a hospital, medical room settings.
10. A single and double shaped hooks attached to sides of the organizer tray structure to facilitate securing medical devices such as stethoscopes, bed-pans, urinal pans, ice bags, hot water bags or other medical and non-medical portable devices.
11. Provides a means for locating in a readily accessible manner a variety of medical paraphernalia.
12. A plurality of recessed varying diameter circular openings for receiving and supporting cylindrical objects, such as drinking cups, pill cups, cold containers for drinks, etc.
13. Rectangular shaped recessed opening for securing appliances such as syringes, scissors, and re-usable supplies such as surgical tape, packets of alcohol wipes, etc.
14. Kidney-shaped recessed opening for device such as emesis basin.
15. Square or rectangular shaped recessed opening for tissue box.
16. A power supply cable entry point providing a 110 volt socket outlet 56.

FIGS. 3, 4 and 5 comprises a plurality of features to achieve the desired invention objectives and by way of enabling disclosure these are identified in the following:
1. The availability of the relevant features 1-6 detailed in [0065].
2. Provision of ready accessibility to a plurality of electrical and electronic devices such as flip-up mirrors 74 with side LED illumination means 68, free-standing swivel LED type light 66 means, FireWire outlet, 64, etc.

It will be evident to those skilled in the art that other changes and modifications from those disclosed herein are possible. The instant invention therefore should not be considered limited to the examples selected for the purpose of illustration, and should be viewed as including all changes and modifications which do not constitute a departure from the essential inventive concept and scope of the instant invention as claimed in the foregoing claims and such equivalents as may be considered appropriate.

We claim:
1. An organizer tray for medical patients, which comprises:
a) the organizer tray having a flat bottom surface, an upper flat top surface, with side portions extending between the flat bottom surface and the upper flat top surface about an outer periphery of the organizer tray, an upstanding rim extending about the outer periphery above the flat surface, a plurality of shaped recesses extending from the upper flat top surface towards the flat bottom surface within the outer periphery of the organizer tray, each shaped recess with sides and a bottom to contain selected items placed therein, the bottom of each shaped recess not extending below the flat bottom surface of the organizer tray, the shaped recesses sized to receive selected COTS items, expendable medical supplies and personal items placed therein, to add stability, security and organization to the placement of the items; and, b) an attachment means for connecting the organizer tray to at least one of: a vertical intravenous (IV) pole; a hospital bed rail; an overbed table; and a nightstand; and, c) wherein at least one Firewire port is located on the outer periphery of the organizer tray; and, d) wherein a mirror is attached to the organizer tray and further wherein the said mirror is lighted; and, e) wherein the said shaped recesses include the capability to accommodate a plurality of shapes; and, f) the recesses provide upstanding rims capable of securing different shaped items; and, g) wherein one or more hooks are attached to the outer periphery of the organizer tray, and the hooks are sized to support various items thereon, including a range of appliances such as, stethoscope, bed pan, catheter bag, ice bag, hot water bag, and a variety of non-medical personal devices; and, h) wherein the hooks are on the same plane as the tray bottom surface and do not extend below the flat bottom surface of the organizer tray, and, i) wherein at least one of the hooks is arranged to be rotated to the side when the organizer tray is placed on a flat surface.

2. The organizer tray of claim 1, wherein the organizer tray is formed by injection molding a suitable material within a selected mold pattern.

3. The organizer of claim 1, wherein the organizer tray is formed from one of: stainless steel, aluminum, and metallic alloy materials, which comprise non-surface oxidizing properties.

4. The organizer tray of claim 1, wherein at least one 110 volt power outlet is located on the outer periphery of the organizer tray.

5. The organizer tray of claim 1, wherein at least one USB port is located on the outer periphery of the organizer tray.

6. The organizer tray of claim 4, wherein a suitable power cord is used to connect the 110 volt power outlet to a remote power outlet on the IV pole, without touching the floor.

7. An organizer tray for medical patients, which comprises:
a) the organizer tray having a flat bottom surface, an upper flat top surface, with side portions extending between the flat bottom surface and the upper flat top surface about an outer periphery of the organizer tray, an upstanding rim extending about the outer periphery above the flat surface, a plurality of shaped recesses extending from the upper flat top surface towards the flat bottom surface within the outer periphery of the organizer tray, each shaped recess with sides and a bottom to contain selected items placed therein, the bottom of each shaped recess not extending below the flat bottom surface of the organizer tray, the shaped recesses sized to receive selected COTS items, expendable medical supplies and personal items placed therein, to add stability, security and organization to the placement of the items; and, b) an attachment means for connecting the organizer tray to at least one of: a vertical intravenous (IV) pole; a hospital bed rail; an overbed table; and a nightstand; and, c) at least one 110 volt power outlet is located on the outer periphery of the organizer tray; and, d) at least one USB port is located on the outer periphery of the organizer tray; and, e) wherein at least one Firewire port is located on the outer periphery of the organizer tray; and, f) wherein a mirror is attached to the organizer tray and further wherein the said mirror is lighted; and, g) wherein the said shaped recesses include the capability to accommodate a plurality of shapes; and, h) the recesses provide upstanding rims capable of securing different shaped items; and, i) wherein one or more hooks are attached to the outer periphery of the organizer tray, and the hooks are sized to support various items thereon, such as a stethoscope, bed pan, catheter bag, ice bag, hot water bag, and a variety of non-medical personal devices, and the said the hooks are on the same plane as the tray bottom surface and do not extend below the flat bottom surface of the organizer tray, and, j) wherein one of the hooks is arranged to be rotated to the side when the organizer is placed on a flat surface.

8. The organizer tray of claim 7, wherein the organizer tray is formed by injection molding a suitable material within a selected mold pattern.

9. The organizer tray of claim 7, wherein the organizer tray is formed from one of: stainless steel, aluminum, and metallic alloy materials, which comprise non-surface oxidizing properties.

10. The organizer tray of claim 7, wherein a suitable power cord is used to connect the 110 volt power outlet to a remote power outlet on the IV pole, without touching the floor.

11. An organizer tray for medical patients, which comprises:
a) the organizer tray having a flat bottom surface, an upper flat top surface, with side portions extending between the flat bottom surface and the upper flat top surface about an outer periphery of the organizer tray, an upstanding rim extending about the outer periphery above the flat surface, a plurality of shaped recesses extending from the upper flat top surface towards the flat bottom surface within the outer periphery of the organizer tray, each shaped recess with sides and a bottom to contain selected items placed therein, the bottom of each shaped recess not extending below the flat bottom surface of the organizer tray, the shaped recesses sized to receive selected COTS items, expendable medical supplies and personal items placed therein, to add stability, security and organization to the placement of the items; and, b) an attachment means for connecting the organizer tray to at least one of: a vertical intravenous (IV) pole; a hospital bed rail; an overbed table; and a nightstand; and, c) at least one 110 volt power outlet is located on the outer periphery of the organizer tray; and, d) at least one USB port is located on the outer periphery of the organizer tray; and, e) at least one Firewire port is located on the outer periphery of the organizer tray; and, f) a suitable power cord is used to connect the 110 volt power outlet to a remote power outlet on the IV pole, without touching the floor; and, g) wherein a mirror is attached to the organizer tray and further wherein the said mirror is lighted; and, h) wherein the said shaped recesses include the capability to accommodate a plurality of shapes, and, i) the recesses provide upstanding rims capable of securing different shaped items, and, i) wherein one or more hooks are attached to the outer periphery of the organizer tray, and the hooks are sized to support various items thereon, and, j) wherein the said hooks are on the same plane as the tray bottom and do not extend below the flat bottom surface of the organizer tray, and, k) wherein at least one of the hooks is arranged to be rotated to the side when the organizer tray is placed on a flat surface.

12. An organizer tray for medical patients, which comprises:
   a) the organizer tray having a flat bottom surface, an upper flat top surface, with side portions extending between the flat bottom surface and the upper flat top surface about an outer periphery of the organizer tray, an upstanding rim extending about the outer periphery above the flat surface, a plurality of shaped recesses extending from the upper flat top surface towards the flat bottom surface within the outer periphery of the organizer tray, each shaped recess with sides and a bottom to contain selected items placed therein, the bottom of each shaped recess not extending below the flat bottom surface of the organizer tray, the shaped recesses sized to receive selected COTS items, expendable medical supplies and personal items placed therein, to add stability, security and organization to the placement of the items; and,
   b) an attachment means for connecting the organizer tray to at least one of: a vertical intravenous (IV) pole; a hospital bed rail; an overhead table; and a nightstand, and,
   c) wherein the said shaped recesses include the capability to accommodate a plurality of shapes, and,
   d) the recesses provide upstanding rims capable of securing different shaped items; and,
   e) wherein one or more hooks are attached to the outer periphery of the organizer tray, and the hooks are sized to support various items thereon, including a range of appliances such as, stethoscope, bed pan, catheter bag, ice bag, hot water bag, and a variety of non-medical personal devices; and,
   f) wherein the hooks are on the same plane as the tray bottom surface and do not extend below the flat bottom surface of the organizer tray, and,
   g) wherein at least one of the hooks is arranged to be rotated to the side when the organizer tray is placed on a flat surface.

13. The organizer tray of claim 12, wherein the organizer tray is formed by injection molding a suitable material within a selected mold pattern.

14. The organizer of claim 12, wherein the organizer tray is formed from one of: stainless steel, aluminum, and metallic alloy materials, which comprise non-surface oxidizing properties.

* * * * *